(12) United States Patent
Liu

(10) Patent No.: US 9,333,311 B2
(45) Date of Patent: May 10, 2016

(54) ELECTRONIC CIGARETTE AND ELECTRONIC CIGARETTE DEVICE

(75) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 729 days.

(21) Appl. No.: 13/697,002

(22) PCT Filed: Aug. 31, 2012

(86) PCT No.: PCT/CN2012/080843
§ 371 (c)(1),
(2), (4) Date: Nov. 8, 2012

(87) PCT Pub. No.: WO2014/032275
PCT Pub. Date: Mar. 6, 2014

(65) Prior Publication Data
US 2014/0060527 A1    Mar. 6, 2014

(51) Int. Cl.
*A24F 47/00* (2006.01)
*A61M 15/06* (2006.01)
*A61M 16/00* (2006.01)

(52) U.S. Cl.
CPC .............. *A61M 15/06* (2013.01); *A24F 47/008* (2013.01); *A61M 2016/0039* (2013.01); *A61M 2205/3375* (2013.01); *A61M 2205/8206* (2013.01); *A61M 2205/8237* (2013.01)

(58) Field of Classification Search
CPC ............... A24F 47/002–47/008; A24F 15/00; A61M 15/06; A61M 2205/0039; A61M 2205/3375; A61M 2205/8206; A61M 2205/8237

USPC ............... 131/270, 273, 194; 128/202.21
See application file for complete search history.

(56) References Cited

U.S. PATENT DOCUMENTS

| | | | | |
|---|---|---|---|---|
| 2,479,895 | A * | 8/1949 | Bahnson, Jr. | 239/123 |
| 2,519,200 | A * | 8/1950 | Schumann | 239/412 |
| 4,298,338 | A * | 11/1981 | Babington | 431/352 |
| 5,113,905 | A * | 5/1992 | Pruitt et al. | 137/571 |
| 2002/0146242 | A1* | 10/2002 | Vieira | 392/395 |
| 2006/0196518 | A1* | 9/2006 | Hon | 131/360 |
| 2010/0242974 | A1* | 9/2010 | Pan | 131/273 |
| 2012/0260927 | A1* | 10/2012 | Liu | 131/329 |

FOREIGN PATENT DOCUMENTS

WO    WO 2012065310    *    5/2012

* cited by examiner

*Primary Examiner* — Michael H Wilson
*Assistant Examiner* — Yana B Krinker
(74) *Attorney, Agent, or Firm* — Cheng-Ju Chiang

(57) ABSTRACT

This invention discloses an electronic cigarette and an electronic cigarette device, the electronic cigarette includes a cartridge and a power unit, the cartridge defines atomizing chambers therein, the power unit includes a power supply therein, the atomizing chambers are mutually parallel to each other, the electronic cigarette further comprises a controller connecting the power supply and the atomizing chambers to control the atomizing chambers to work. The electronic cigarette and the electronic cigarette device of the invention have multiple atomizing chambers parallel to each other, and the controller which connects the power supply and the atomizing chambers to control the atomizing chambers to work, thereby achieving big and thick smoke for good flavor. On the other hand, the atomizing chambers accommodate different types of smoke oils, this makes the electronic cigarette to generate smoke with multiple mixed flavors, thus, the users can change the flavors of smoke as they like.

12 Claims, 4 Drawing Sheets

ELECTRONIC CIGARETTE AND ELECTRONIC CIGARETTE DEVICE

CROSS REFERENCE TO RELATED APPLICATIONS

The present application is a 35 U.S.C. §371 National Phase conversion of International (PCT) Patent Application No. PCT/CN2012/080843, filed on Aug. 31, 2012, the disclosure of which is incorporated by reference herein. The PCT International Patent Application was filed in Chinese.

TECHNICAL FIELD

This invention relates to an electronic cigarette and an electronic cigarette device.

DESCRIPTION OF BACKGROUND

Electronic cigarettes are a kind of simulating cigarettes which heat and atomize materials having flavors through heating wire to generate smoke for users' suction. Current electronic cigarettes usually have only one atomizing chamber, the smoke generated in the atomizing chamber is small, with lighter taste.

In addition, current electronic cigarettes have single taste, which cannot meet users' multi-flavor needs.

SUMMARY

An object of the present invention is to provide an electronic cigarette and an electronic cigarette device which can generate big and thick smoke with good flavor.

Another object of the present invention is to provide an electronic cigarette and an electronic cigarette device which can generate multiple mixed-favor smoke, so that users can change the flavors of smoke as they like.

To achieve the above objects, the present invention provides an electronic cigarette, comprising a cartridge and a power unit, the cartridge defining atomizing chambers therein, the power unit comprising a power supply therein, the atomizing chambers being mutually parallel to each other, and the electronic cigarette further comprising a controller which connects the power supply and the atomizing chambers to control the atomizing chambers to work.

Furthermore, the controller comprises: a switch unit which generates a trigger signal in response to an external operation; and an integrated circuit electrically connecting to the switch unit and achieving an electrical connection of the power supply to the atomizing chambers according to the trigger signal.

Furthermore, the switch unit is a micro-mechanical switch or an air flow sensor.

Furthermore, each atomizing chamber is defined in an atomizer, and the atomizers are mutually parallel to each other.

Furthermore, the atomizing chambers accommodate liquid smoke oils, and types of the smoke oils are different from each other.

Furthermore, the cartridge comprises a nozzle, atomizers configured within the nozzle, a nozzle cover disposed at an end of the nozzle, and a first connecting collar disposed at another end of the nozzle for engaging with the power unit.

Furthermore, the power unit comprises a power sheath, a power supply disposed in the power sheath, a second connecting collar disposed at an end of the power sheath and fittingly connected to the first connecting collar and an end cap disposed at another end of the power sheath.

Furthermore, the second connecting collar is fixedly provided with a fixing holder therein, and the switch unit is secured onto the fixing holder.

Furthermore, the integrated circuit is disposed on a circuit board, and the circuit board is fixed on the fixing holder and electrically connected to the switch unit.

Furthermore, the second connecting collar in its end which corresponds to the cartridge defines connecting tunnels which are consistent with the atomizers in number, and the connecting tunnels are provided with inner thread, and the atomizers are provided with outer thread at an end thereof to correspondingly engage with the inner thread.

Furthermore, the atomizers each comprise a shell, a tubular smoke oil reservoir disposed within the shell, a filling layer disposed between the smoke oil reservoir and the shell, a lid disposed at an end of the shell and fittingly sealing an end port of the smoke oil reservoir, and a seat disposed at another end of the shell and fittingly sealing another end port of the smoke oil reservoir, and said another end of the shell is provided with outer thread.

Furthermore, a first electrode is provided within each of the connecting tunnels and coaxial with the corresponding connecting tunnel, and configured to be electrically connected to the circuit board and the corresponding atomizer; and the smoke oil reservoir accommodates smoke oil therein and is provided with heating wires, and a second electrode is provided within the seat, coaxial with the seat to couple with its corresponding first electrode, and electrically connected with its corresponding the heating wire.

Furthermore, a sealed chamber in the smoke oil reservoir, the smoke oil accommodated in the sealed chamber and the heating wire disposed in the sealed chamber construct the atomizing chamber.

Furthermore, a first insulating sleeve is configured between the first electrode and the corresponding connecting tunnel, and a second insulating sleeve is configured between the second electrode and a port of said another end of the shell.

Correspondingly, the present invention further provides an electronic cigarette device which comprises the above-said electronic cigarette and an electronic cigarette casing for accommodating and charging the electronic cigarette.

The technical advantages of the electronic cigarette and the electronic cigarette device in the invention are: the multiple atomizing chambers disposed in a parallel manner, and the controller connecting the power supply and the atomizing chambers to control the work of the atomizing chambers, can thus make the electronic cigarette to achieve big and thick smoke for good flavor. In addition, the atomizing chambers accommodate different types of smoke oils, this makes the electronic cigarette to generate smoke with multiple mixed flavors, thus, the users can change the flavors of smoke as they like.

DETAILED DESCRIPTION OF THE EMBODIMENTS

Figure 1:
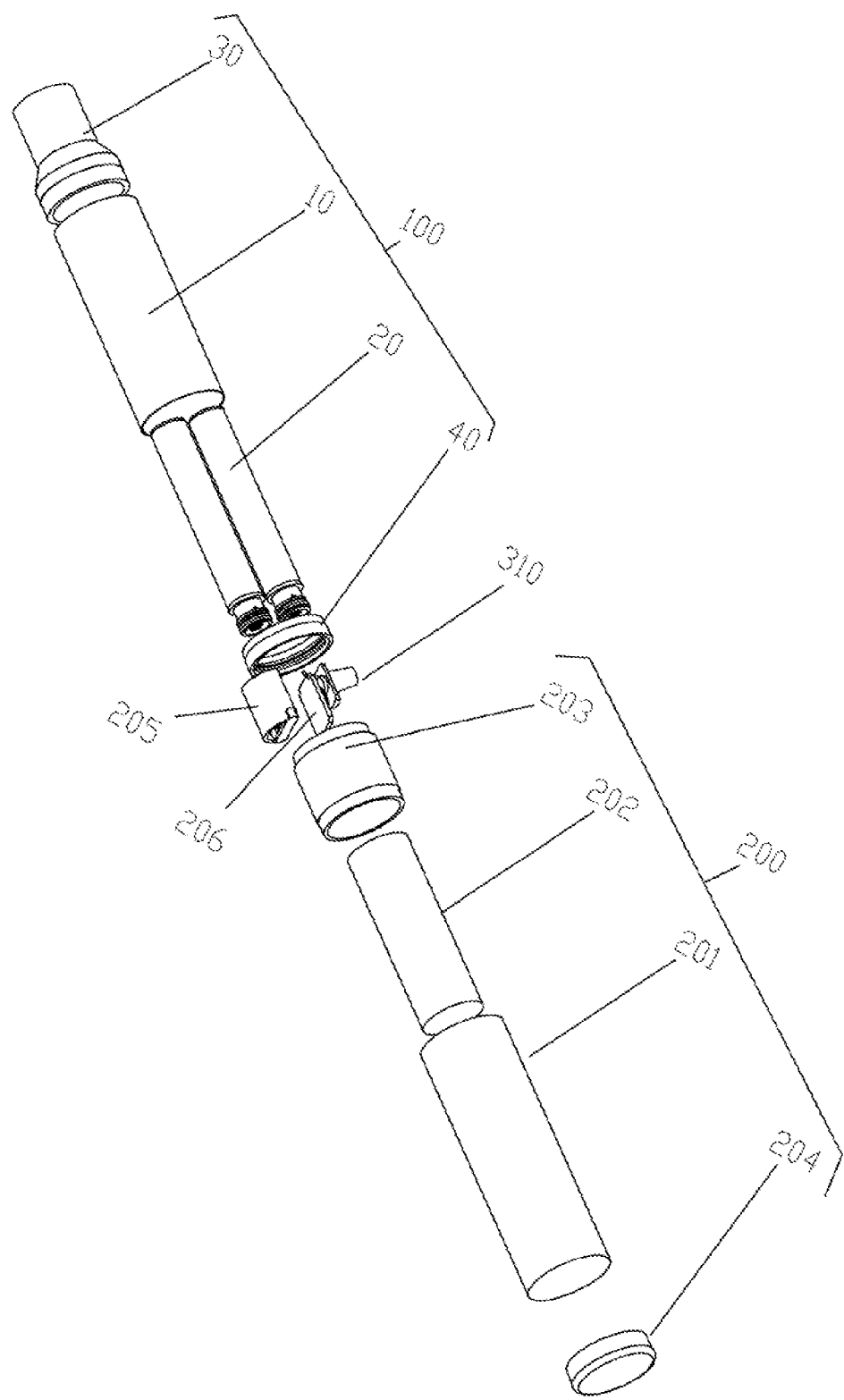
FIG. 1 is an exploded view of an electronic cigarette in accordance with an embodiment of the present invention.

As shown in FIGS. 1-5, an electronic cigarette and an electronic cigarette device are provided in accordance with embodiments of the present invention. The electronic cigarette device comprises an electronic cigarette and an electronic cigarette casing for accommodating and charging the electronic cigarette.

The electronic cigarette provided in the embodiments of the present invention, comprises a cartridge 100, a power unit 200 and a controller 300. The cartridge 100 comprises a nozzle 10, at least two atomizers 20, a nozzle cover 30 and a first connecting collar 40.

The nozzle 10 is in a tubular shape.

The atomizers 20 are configured within the cartridge 100, specifically within the nozzle 10, and the atomizers 20 are disposed in a manner that they are mutually parallel to each other. Each atomizer 20 is equipped with an atomizing chamber, and the atomizing chambers are also disposed in the manner that they are mutually parallel to each other, and the atomizing chambers accommodate liquid smoke oils therein. In one embodiment, the types of the smoke oils in all of the atomizing chambers are same, therefore, the controller 300 is capable of controlling one or more atomizing chambers to increase the amount of smoke to get better taste; in another embodiment, the types of the smoke oils in the atomizing chambers are different from each other, for example, the smoke oils respectively are of cigar flavor, Hongta® flavor, and Chung Hwa® flavor, etc. Therefore, the atomizing chambers can accommodate different types of smoke oils, to provide the users with multiple mixed flavors.

Figure 4:
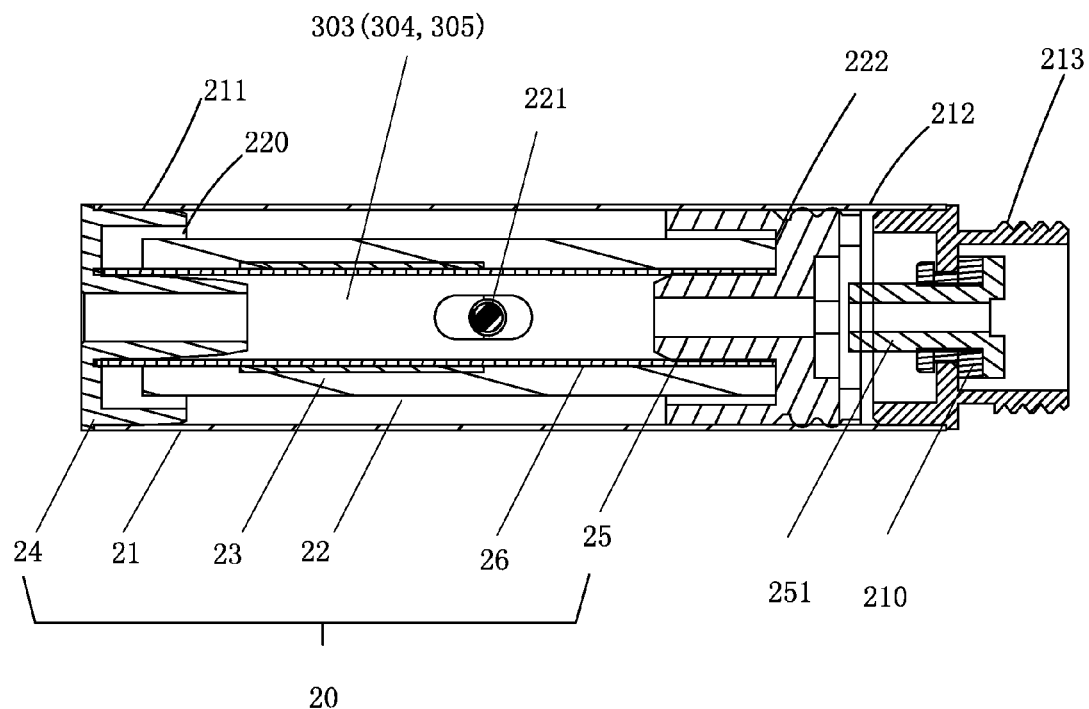
FIG. 4 is a cross-sectional view of an atomizer of an electronic cigarette in accordance with an embodiment of the present invention.

Referring to FIG. 4, each atomizer 20 separably comprises a shell 21, a smoke oil reservoir 22, a filling layer 23 for storing smoke oil in the reservoir 22, a lid 24, a seat 25, and a tube 26.

The shell 21 is tubular, and the shell 21 is made of steel material.

The smoke oil reservoir 22 is tubular, and disposed within the shell 21. In the embodiment, the smoke oil reservoir 22 is defined between the shell 21 and the tube 26, and the tube 26 is a fiberglass tube, and the smoke oil reservoir 22 accommodates smoke oil therein and is provided with one or more heating wires 221 in the tube 26.

The filling layer 23 is disposed between in the smoke oil reservoir 22 and the shell 21, and the filling layer 23 is embodied as cotton breathable material having buffering and breathable function.

The lid 24 is disposed at a first end 211 of the shell 21, and fittingly seals a first end port 220 of the smoke oil reservoir 22.

Each seat 25 is disposed within a second end 212 of the corresponding shell 21, and fittingly seals a second end port 222 of the smoke oil reservoir 22. The second end 212 of each shell 21 is provided with outer thread 213.

The nozzle cover 30 is disposed at a first end 11 of the nozzle 10, for facilitating users' suction.

The first connecting collar 40 is disposed at a second end 12 of the nozzle 10, for engaging with the power unit 200.

The power unit 200 comprises a power sheath 201, a power supply 202, a second connecting collar 203 and an end cap 204.

The power sheath 201 is tubular, and is made of steel material.

The power supply 202 is disposed in the power sheath 201, and the power supply 202 is for example a rechargeable battery or a disposable battery.

The second connecting collar 203 is disposed at an end of the power sheath 201, and fittingly connected to the first connecting collar 40. A fixing holder 205 for support is secured in the second connecting collar 203. The fixing holder 205 is fixedly provided with a circuit board 206 thereon, and the circuit board 206 is connected to the power supply 202. The second connecting collar 203 in its end which corresponds to the cartridge 100 defines at least two connecting tunnels 207 which are consistent with the atomizers 20 in number. A first electrode 208 is provided within each of the connecting tunnels 207 and coaxial with the corresponding connecting tunnel 207; and the first electrode 208 is configured to be electrically connected to the circuit board 206 and the corresponding atomizer 20. Each of the connecting tunnels 207 is provided with inner thread, and each of the atomizers 20 is provided with the outer thread 213 at the second end 212 thereof to correspondingly engage with the inner thread, therefore, the atomizers 20 are secured to the power unit 200. Correspondingly, a second electrode 251 is provided within each seat 25 at the second end 212 of the shell 21 and coaxial with the seat 25 to couple with its corresponding first electrode 208. The second electrode 251 is electrically connected with the heating wire 221, so that an electronic connection of the atomizer 20, the circuit board 206 and the power supply 202 is achieved through the first electrode 208 and the second electrode 251. Wherein, a sealed chamber is defined in the smoke oil reservoir 22, the smoke oil is accommodated in the sealed chamber between the shell 21 and the tube 26; and each heating wire 221 is disposed in each atomizing chamber 303, 304, 305 defined in each tube 26. A first insulating sleeve 209 is configured between the first electrode 208 and an inner wall of the corresponding connecting tunnel 207, for sealing and electronic insulation. A second insulating sleeve 210 is configured between the second electrode 251 and a port of the second end 212 of the shell 21 of each atomizer 20, for sealing and electronic insulation.

The end cap 204 is disposed at another end of the power sheath 201.

Figure 5:
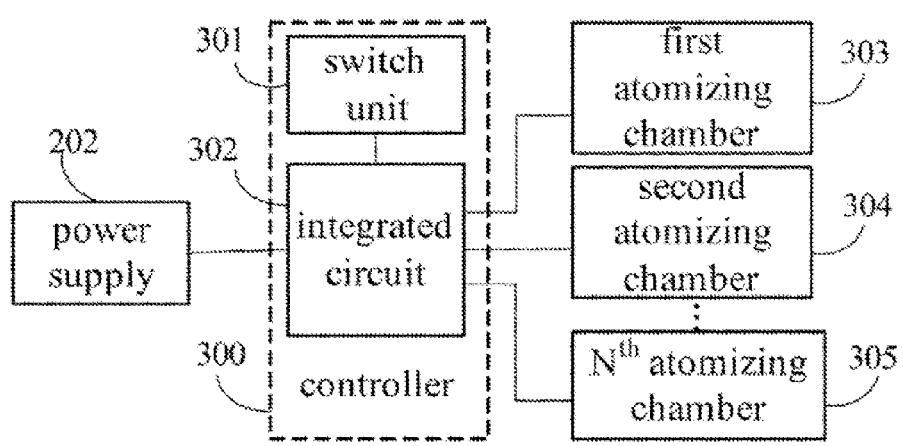
FIG. 5 is a circuit block diagram of an electronic cigarette in accordance with an embodiment of the present invention.

Referring to FIG. 5, the controller 300 connects the power supply 202 and the atomizers 20 so as to control each heating wire 221 in each of the atomizing chambers to work. The controller 300 comprises a switch unit 301 and an integrated circuit (IC) 302. In the embodiment, there are N atomizers 20, respectively, a first atomizing chamber 303, a second atomizing chamber 304, . . . , and an Nth atomizing chamber 305.

Figure 2:
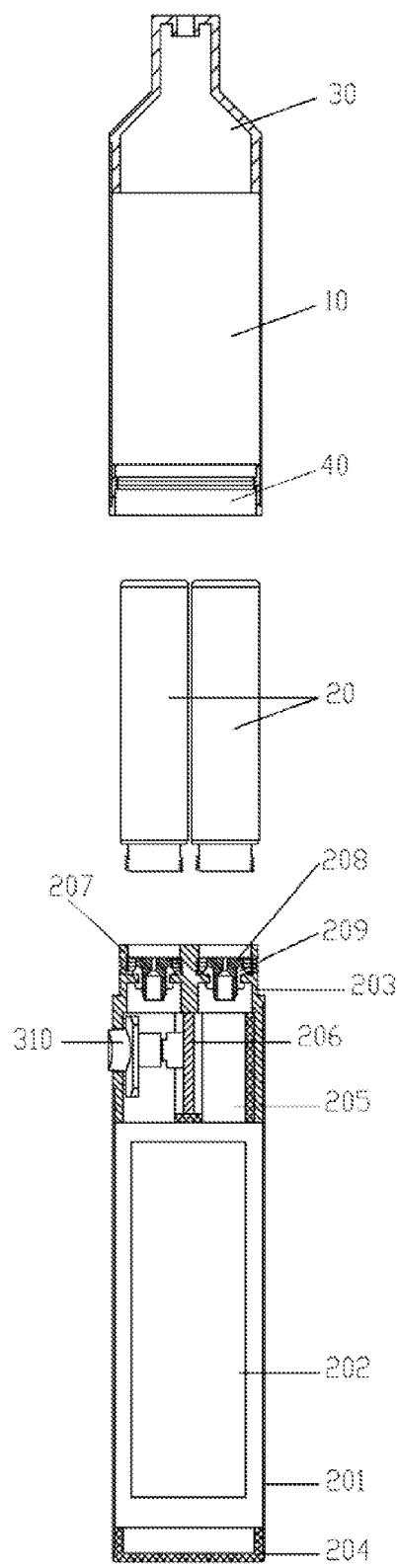
FIG. 2 is a cross-sectional view of the electronic cigarette of FIG. 1.
Figure 3:
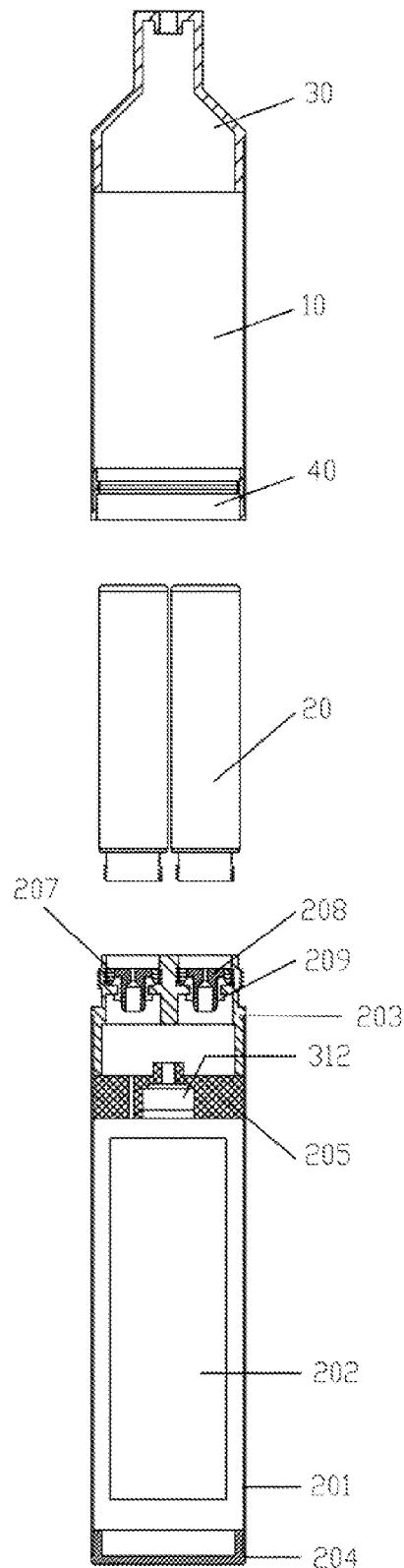
FIG. 3 is a cross-sectional view of an electronic cigarette in accordance with another embodiment of the present invention.

The switch unit 301 is configured to generate a trigger signal in response to an external operation. Specifically, the switch unit 301 is fixedly provided at the fixing holder 205, and the switch unit 301 is, for example, a micro-mechanical switch 310 as shown in FIG. 2, or an air flow sensor 312, i.e., microphone, as shown in FIG. 3. For the micro-mechanical switch 310, the corresponding trigger signal is generated according to the times or time length of pressing/touching the micro-mechanical switch 310; for the air flow sensor 312, the corresponding trigger signal is generated according to the size of the air flow or the time length of the air flow passing through the air flow sensor 312.

The IC 302 is electrically connected to the switch unit 301, for achieving an electrical connection of the power supply 202 to the atomizing chambers according to the trigger signal. The IC 302 is disposed on the circuit board 206 which is fixed on the fixing holder 205 and electrically connected to the switch unit 301. The IC 302 is pre-stored with or set up by users with multiple control commands corresponding to the trigger signals, for example, the trigger signal generated by the switch unit 301 in response to one pressing of user corresponds to a control command of having the first atomizing chamber 303 and the second atomizing chamber 304 to work simultaneously; the trigger signal generated in response to continuous twice pressing corresponds to a control command of having the first atomizing chamber 303, the second atomizing chamber 304 and a third atomizing chamber (not shown) to work simultaneously. For another example, the trigger signal generated by the switch unit 301 in response to a long pressing of more than 3 seconds corresponds to a control command of having all of the atomizing chambers to work simultaneously, thus, the IC 302 generates the control command corresponding to the trigger signal and the corresponding circuit is conducted according to the control command to have multiple atomizing chambers to work simultaneously and generate big and thick smoke for good flavor. On the other hand, multiple mixed flavors can be achieved by setting of the control commands, exchanging positions of the atomizers 20, or adding/replacing the atomizers 20 accommodating different types of smoke oils.

In summary, the electronic cigarette and the electronic cigarette device of the embodiments of the present invention have multiple atomizing chambers disposed in a parallel manner, and the controller 30 connecting the power supply 202 and the atomizing chambers to control the work of the atomizing chambers, to thus achieve big and thick smoke for good flavor; on the other hand, the atomizing chambers accommodate different types of smoke oils, this makes the electronic cigarette to generate smoke with multiple mixed flavors, thus, the users can change the flavors of smoke as they like.

The above-mentioned is only the embodiments of the present invention. It should be noted, for the persons of ordinary skill in this field, improvements and modifications within the spirit of the present invention can be made, and the improvements and modifications should be seemed to be included in the claimed scope of this invention.

What is claimed is:

1. An electronic cigarette, comprising a cartridge and a power unit;
the cartridge defining atomizing chambers therein, the power unit comprising a power supply therein;
wherein the cartridge therein further comprises at least two mutually parallel and separable atomizers; each atomizer defines one of the atomizing chambers therethrough; the atomizing chambers are mutually parallel to each other accordingly;
each atomizer separably comprises a tubular shell, a tube, a heating wire in the atomizing chamber, a tubular smoke oil reservoir defined between the shell and the tube, a lid, and a seat; the lid and the seat are respectively disposed at a first end and a second end of the shell, and fittingly seal a first end port and a second end port of the smoke oil reservoir;
the electronic cigarette is capable of exchanging positions of the atomizers, adding or replacing the atomizers; and
the electronic cigarette further comprises a controller which connects the power supply and each atomizer to control the heating wire in each of the atomizing chambers.

2. The electronic cigarette as described in claim 1, wherein the controller comprises:
a switch unit which generates a trigger signal in response to an external operation; and
an integrated circuit electrically connected to the switch unit and achieving an electrical connection of the power supply to the atomizing chambers according to the trigger signal.

3. The electronic cigarette as described in claim 2, wherein the switch unit is a micro-mechanical switch or an air flow sensor.

4. The electronic cigarette as described in claim 2, wherein the cartridge comprises a nozzle, atomizers configured within the nozzle, a nozzle cover disposed at a first end of the nozzle, and a first connecting collar disposed at a second end of the nozzle for engaging with the power unit.

5. The electronic cigarette as described in claim 4, wherein the power unit comprises a power sheath, a power supply disposed in the power sheath, a second connecting collar disposed at a first end of the power sheath and fittingly connected to the first connecting collar, and an end cap disposed at a second end of the power sheath.

6. The electronic cigarette as described in claim 5, wherein the second connecting collar is fixedly provided with a fixing holder therein, and the switch unit is secured onto the fixing holder.

7. The electronic cigarette as described in claim 6, wherein the integrated circuit is disposed on a circuit board, and the circuit board is fixed on the fixing holder and electrically connected to the switch unit.

8. The electronic cigarette as described in claim 5, wherein the second connecting collar in its end which corresponds to the cartridge defines connecting tunnels which are consistent with the atomizers in number, and the connecting tunnels are provided with inner thread, and each of the atomizers are provided with outer thread at an end thereof to correspondingly engage with the inner thread.

9. The electronic cigarette as described in claim 8, wherein the second end of the shell is provided with the outer thread of the atomizers.

10. The electronic cigarette as described in claim 8, wherein a first electrode is provided within each of the connecting tunnels and coaxial with the corresponding connecting tunnel, and configured to be electrically connected to the circuit board and the corresponding atomizer; and the smoke oil reservoir accommodates smoke oil therein, and a second electrode is provided at the second end of the shell, coaxial with the seat to couple with its corresponding first electrode, and electrically connected with its corresponding heating wire.

11. The electronic cigarette as described in claim 10, wherein a first insulating sleeve is configured between the first electrode and the corresponding connecting tunnel, and a second insulating sleeve is configured between the second electrode and a port of the second end of the shell.

12. The electronic cigarette as described in claim 1, wherein the smoke oil reservoirs accommodate liquid smoke oils, and the types of the smoke oils are different from each other.

* * * * *